(12) United States Patent
Robles et al.

(10) Patent No.: US 8,859,839 B2
(45) Date of Patent: Oct. 14, 2014

(54) DISPOSABLE WEARABLE ABSORBENT ARTICLES WITH GENDER SPECIFIC INDICATING

(75) Inventors: Miguel Alvaro Robles, Wyoming, OH (US); Donald Carroll Roe, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 960 days.

(21) Appl. No.: 12/646,354

(22) Filed: Dec. 23, 2009

(65) Prior Publication Data
US 2010/0168698 A1     Jul. 1, 2010

Related U.S. Application Data

(63) Continuation-in-part of application No. 12/346,510, filed on Dec. 30, 2008, now abandoned.

(51) Int. Cl.
*A61F 13/42* (2006.01)
*A61F 13/84* (2006.01)

(52) U.S. Cl.
CPC ......... *A61F 13/42* (2013.01); *A61F 2013/8497* (2013.01)
USPC ....................................................... 604/361

(58) Field of Classification Search
CPC   A61F 13/42; A61F 13/491; A61F 2013/8497
USPC ....................................................... 604/361
See application file for complete search history.

(56) References Cited

U.S. PATENT DOCUMENTS

| 4,507,121 | A | 3/1985 | Leung |
| 5,078,708 | A | 1/1992 | Haque |
| 5,435,010 | A | 7/1995 | May |
| 6,297,424 | B1 | 10/2001 | Olson et al. |
| 6,307,119 | B1 | 10/2001 | Cammarota et al. |
| 6,710,221 | B1 | 3/2004 | Pierce et al. |
| 2001/0008683 | A1 | 7/2001 | Takai et al. |
| 2002/0007162 | A1* | 1/2002 | Cammarota et al. .......... 604/361 |
| 2002/0016579 | A1 | 2/2002 | Stenberg |
| 2003/0078553 | A1 | 4/2003 | Wada et al. |
| 2003/0130631 | A1 | 7/2003 | Springer et al. |
| 2004/0138633 | A1* | 7/2004 | Mishima et al. ............... 604/361 |
| 2004/0254550 | A1* | 12/2004 | Huang et al. .................. 604/361 |
| 2005/0065489 | A1 | 3/2005 | Driskell et al. |
| 2005/0148961 | A1* | 7/2005 | Sosalla et al. ................. 604/361 |

(Continued)

FOREIGN PATENT DOCUMENTS

| DE | 85 06 388 U1 | 6/1985 |
| DE | 20 2006 008161 | 3/2007 |

(Continued)

OTHER PUBLICATIONS

U.S. Appl. No. 12/646,296, filed Dec. 23, 2009, Robles, et al.

(Continued)

*Primary Examiner* — Tan-Uyen T Ho
*Assistant Examiner* — Peter S Vasat
(74) *Attorney, Agent, or Firm* — Kathleen Y. Carter; Betty J. Zea; Charles R. Ware

(57) ABSTRACT

A disposable wearable absorbent article including a gender specific visual wetness indicating area.

18 Claims, 6 Drawing Sheets

(56) References Cited

U.S. PATENT DOCUMENTS

| | | |
|---|---|---|
| 2006/0069361 A1* | 3/2006 | Olson .................. 604/361 |
| 2006/0069362 A1 | 3/2006 | Odorzynski et al. |
| 2006/0149197 A1 | 7/2006 | Niemeyer et al. |
| 2006/0149204 A1 | 7/2006 | Niemeyer et al. |
| 2006/0229577 A1 | 10/2006 | Roe et al. |
| 2007/0197986 A1 | 8/2007 | Matsui |
| 2007/0233027 A1* | 10/2007 | Roe et al. ............. 604/361 |
| 2007/0276348 A1* | 11/2007 | Stenberg ............... 604/361 |
| 2008/0086060 A1 | 4/2008 | Kritzman et al. |
| 2008/0147031 A1 | 6/2008 | Long et al. |
| 2008/0208151 A1 | 8/2008 | Zacharias et al. |
| 2008/0228157 A1 | 9/2008 | McKiernan et al. |
| 2010/0168695 A1 | 7/2010 | Robles et al. |
| 2010/0168696 A1 | 7/2010 | Robles et al. |
| 2010/0168697 A1 | 7/2010 | Robles et al. |
| 2010/0168698 A1 | 7/2010 | Robles et al. |
| 2010/0168699 A1 | 7/2010 | Robles et al. |
| 2010/0168700 A1 | 7/2010 | Schmidt et al. |
| 2010/0168701 A1 | 7/2010 | Schmidt et al. |

FOREIGN PATENT DOCUMENTS

| | | |
|---|---|---|
| EP | 0 705 089 B1 | 5/1997 |
| EP | 0 925 769 A2 | 6/1999 |
| EP | 1 216 673 B1 | 10/2005 |
| FR | 2 695 824 B1 | 3/1994 |
| JP | 2001-095845 | 4/2001 |
| JP | 2005-127933 A2 | 5/2005 |
| KR | 98039173 | 8/1998 |
| KR | 100484478 B1 | 4/2005 |
| WO | WO 95/00099 A1 | 1/1995 |
| WO | WO 99/56690 A1 | 11/1999 |
| WO | WO 01/95845 A1 | 12/2001 |
| WO | WO 2005/030084 A2 | 4/2005 |
| WO | WO 2005/039656 A1 | 5/2005 |
| WO | WO 2005/102238 A1 | 11/2005 |
| WO | WO 2006/110428 A1 | 10/2006 |
| WO | WO 2008/072116 A1 | 6/2008 |

OTHER PUBLICATIONS

U.S. Appl. No. 12/646,315, filed Dec. 23, 2009, Robles, et al.
U.S. Appl. No. 12/646,334, filed Dec. 23, 2009, Robles, et al.
U.S. Appl. No. 12/646,393, filed Dec. 23, 2009, Robles, et al.
U.S. Appl. No. 12/646,414, filed Dec. 23, 2009, Schmidt, et al.
U.S. Appl. No. 12/646,430, filed Dec. 23, 2009, Schmidt, et al.
Lambi Premium Diapers manufactured by Lambi, Mexico as advertised for sale on the Bella Baby Boutique website on Apr. 30, 2009 shown in size Large.
International Search Report, PCT/US2009/069569, mailed May 19, 2010, 17 pages.
International Search Report, PCT/US2009/069559, mailed Feb. 17, 2010, 12 pages.
International Search Report, PCT/US2009/069579, mailed Apr. 22, 2010, 12 pages.
International Search Report, PCT/US2009/069570, mailed Apr. 22, 2010, 12 pages.
International Search Report, PCT/US2009/069572, mailed May 7, 2010, 16 pages.
International Search Report, PCT/US2009/069659, mailed Jun. 7, 2010, 17 pages.
International Search Report, PCT/US2009/069656, mailed Jun. 7, 2010, 17 pages.

* cited by examiner

DISPOSABLE WEARABLE ABSORBENT ARTICLES WITH GENDER SPECIFIC INDICATING

CROSS REFERENCE TO RELATED APPLICATIONS

This application is a continuation-in-part of U.S. application Ser. No. 12/346,510, filed Dec. 30, 2008 now abandoned, the substance of which is hereby incorporated by reference.

FIELD

In general, embodiments of the present disclosure relate to wetness indicating for absorbent articles. In particular, embodiments of the present disclosure relate to visual fullness indicating for disposable wearable absorbent articles.

BACKGROUND

Disposable wearable absorbent articles can absorb liquid bodily exudates such as urine. A disposable wearable absorbent article can include a wetness indicator. The wetness indicator can indicate the presence of a liquid bodily exudate in the article. Unfortunately, some wetness indicators for absorbent articles can be difficult to understand, since the gender of the wearer can affect an indicator's signal. If the signal from a wetness indicator is misunderstood then the absorbent article may be changed too soon. The wearer may underutilize the capacity of the article. If the signal from a wetness indicator is misunderstood then the absorbent article may be changed too late. The bodily exudates may exceed the capacity of the article resulting in leaks.

SUMMARY

Figure 1A:
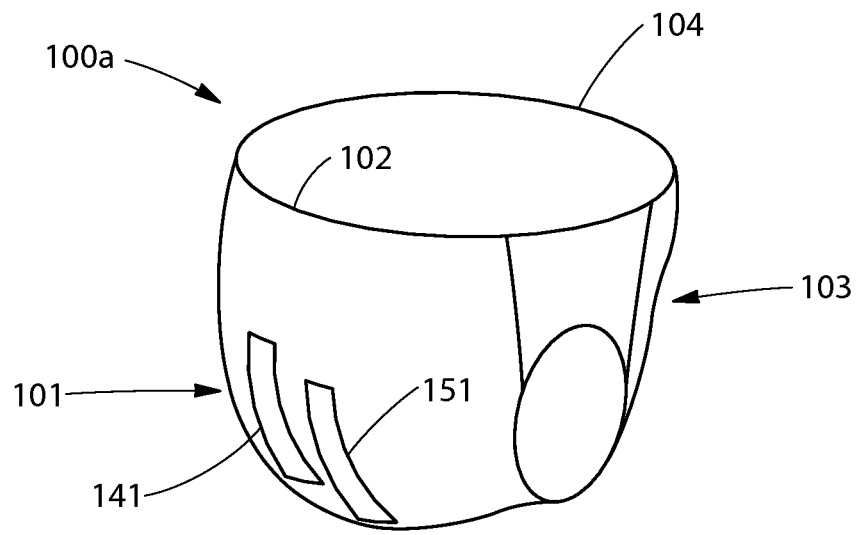
FIG. 1A illustrates a pant-type disposable wearable absorbent article with gender specific visual wetness indicators in the front, according to embodiments of the present disclosure.

The present disclosure includes absorbent articles with wetness indicators that are easy to understand. The absorbent articles of the present disclosure are easy to understand because they have gender specific indicators.

As an example, an absorbent article can have a visual fullness indicator configured for a male wearer and a visual fullness indicator configured for a female wearer. These indicators can be positioned in the article to account for a wearer's gender. When the article is worn by a male, the fullness of the absorbent article can be determined by observing a change in visual state in the visual fullness indicator configured for a male wearer. When the article is worn by a female, the fullness of the absorbent article can be determined by observing by a change in visual state in the visual fullness indicator configured for a female wearer. An absorbent article with visual fullness indicators configured for male and female wearers can be easily understood as providing gender specific wetness indicating.

An absorbent article with gender specific wetness indicating can help provide certainty about the fullness of the absorbent article for a wearer of a particular gender. By knowing how full an article is, the article can be changed after the wearer has appropriately utilized the capacity of the article. Also, by knowing how full an article is, the article can be changed before it is likely to leak.

DETAILED DESCRIPTION

The gender specific indicators of the present disclosure can be used with all kinds of absorbent articles. An absorbent article can absorb liquid bodily exudates such as sweat, blood, urine, menses, etc. An absorbent article can be a product or a material. Examples of absorbent articles include products and/or materials for sanitary protection, hygienic use, and/or wound care.

Some absorbent articles are disposable. A disposable absorbent article is configured to be partly or wholly disposed of after a single use. A disposable absorbent article is configured such that the soiled article, or a soiled portion of the article, is not intended to be restored and reused (e.g., not intended to be laundered). Examples of disposable absorbent articles include wound care products, such as bandages and dressings, as well as feminine care products, such as pads and liners. Disposable absorbent articles can use embodiments of the present disclosure.

Some absorbent articles are wearable. A wearable absorbent article is configured to be worn on or around a body of a wearer. Wearable absorbent articles can also be disposable. Examples of disposable wearable absorbent articles include disposable diapers and disposable incontinence undergarments. A disposable wearable absorbent article can receive and contain bodily exudates while being worn by a wearer. In some embodiments, a disposable wearable absorbent article can include a topsheet, an absorbent core, an outer cover, a waist opening, and leg openings. Disposable wearable absorbent articles can use embodiments of the present disclosure.

One kind of wetness indicator for an absorbent article is a visual fullness indicator. A wetness indicator is considered visual if it can indicate the presence of a liquid bodily exudate by its visual state. Throughout the present disclosure, unless otherwise stated, the presence of a liquid bodily exudate refers to the presence of a concentration of the liquid bodily exudate that is sufficient to cause a visual wetness indicator to change visual states. A wetness indicator is considered a fullness indicator if it can indicate the degree to which a liquid bodily exudate has filled an absorbent article. A visual fullness indicator can indicate the presence of a liquid bodily exudate by a wet edge that moves along the indicator such that the indicator progressively changes visual states. A visual fullness indicator can include one or more visual fullness indicating areas. An indicating area is a defined continuous two-dimensional region, configured to indicate the presence of a liquid bodily exudate by its visual state. As examples, in various embodiments, an indicator can comprise a series of indicating areas or a pattern of indicating areas.

The figures of the present disclosure are intended to illustrate elements, their parts, and their relationships, as described in the specification; the figures are not intended to illustrate any particular relative or absolute size or dimension, unless otherwise stated in the text.

FIGS. 1A-2C illustrate various disposable wearable absorbent articles, each with one or more gender specific indicators. For clarity, FIGS. 1A-2C do not illustrate all details of the indicators or of the disposable wearable absorbent articles. Each indicator in FIGS. 1A-2C can be any embodiment of an indicator of the present disclosure.

FIG. 1A illustrates an outside perspective view of a front 101 and a side 103 of a pant-type disposable wearable absorbent article 100A formed for wearing. The pant-type disposable wearable absorbent article 100A includes a waist opening 107 and a leg opening 108. The absorbent article 100A includes a front waist edge 102 and a back waist edge 104. The absorbent article 100A also includes a longitudinally oriented visual fullness indicator 141 configured for a male wearer and a longitudinally oriented visual fullness indicator 151 configured for a female wearer, both disposed in the front 101.

Throughout the present disclosure, a reference to a pant-type disposable wearable absorbent article can refer to an embodiment that is side-fastenable or to an embodiment without fasteners. A reference to a pant-type disposable wearable absorbent article can also refer to an article with pre-formed waist and/or leg openings or to an embodiment that is not preformed. Thus, each embodiment of an absorbent article of the present disclosure that is described as pant-type can be configured in any of these ways, as will be understood by one of ordinary skill in the art.

Figure 1B:
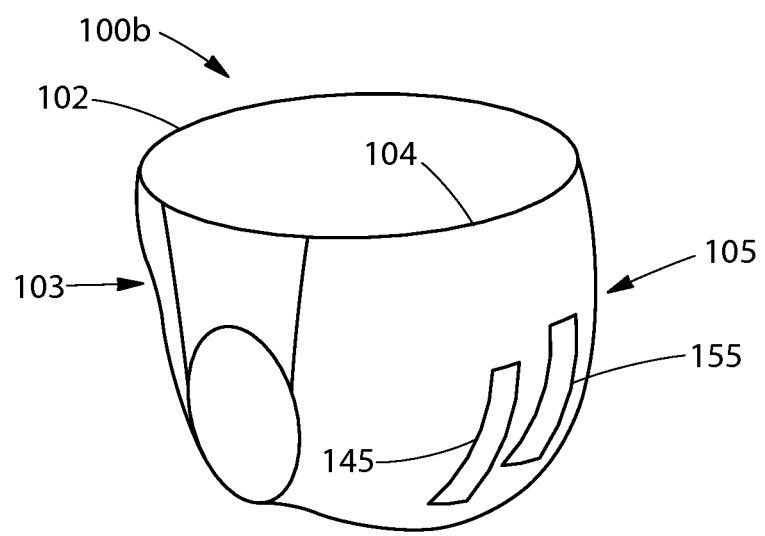
FIG. 1B illustrates a pant-type disposable wearable absorbent article with gender specific visual wetness indicators in the back, according to embodiments of the present disclosure.

FIG. 1B illustrates an outside perspective view of a side 103 and a back 105 of an pant-type disposable wearable absorbent article 100B formed for wearing. The pant-type disposable wearable absorbent article 100B includes a waist opening 107 and a leg opening 108. The absorbent article 100B includes a front waist edge 102 and a back waist edge 104. The absorbent article 100B also includes a longitudinally oriented visual fullness indicator 145 configured for a male wearer and a longitudinally oriented visual fullness indicator 155 configured for a female wearer, both disposed in the back 105.

Figure 1C:
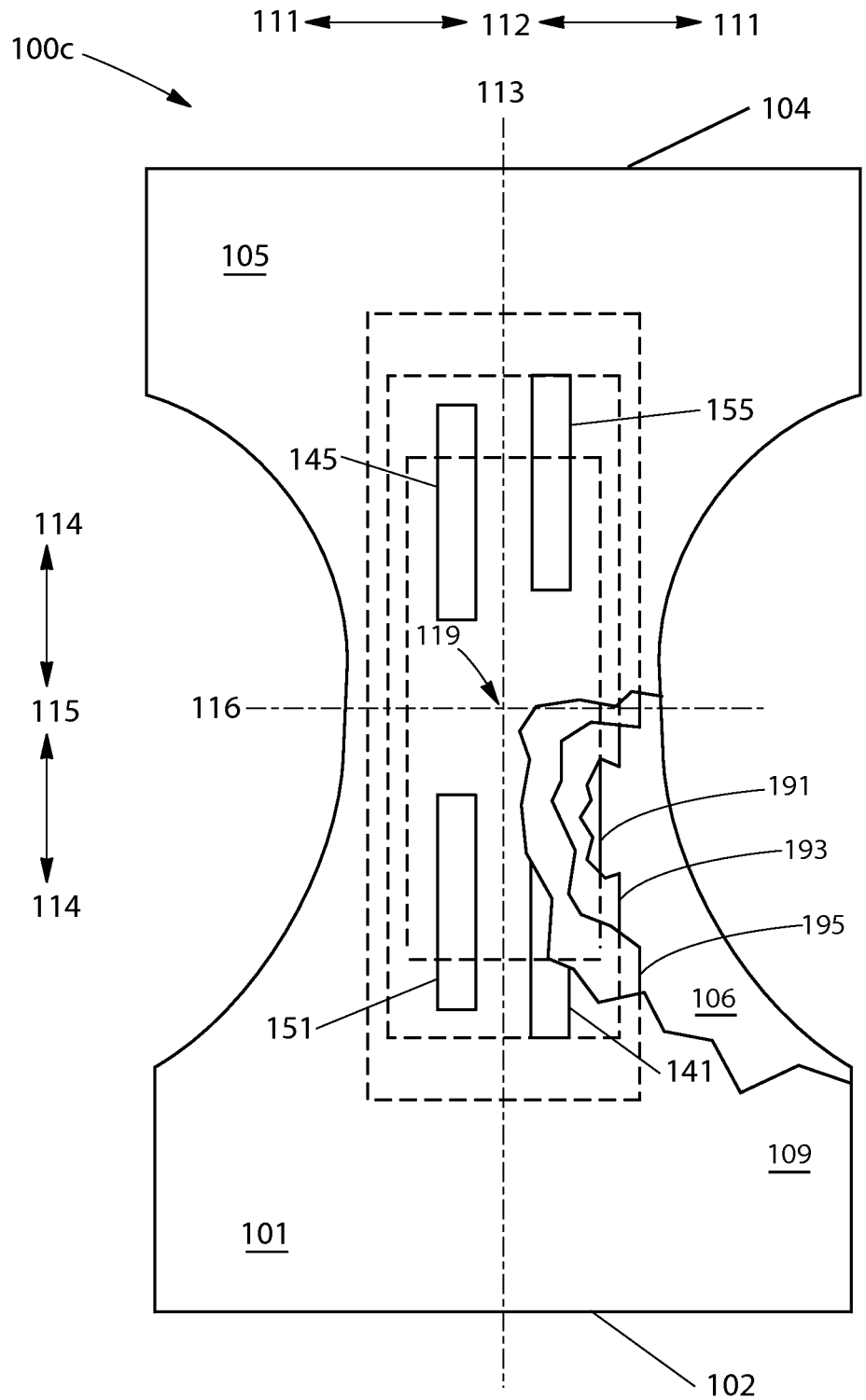
FIG. 1C illustrates a pant-type disposable wearable absorbent article with a number of gender specific visual wetness indicators, according to embodiments of the present disclosure.

FIG. 1C illustrates an outside plan view of a pant-type disposable wearable absorbent article 100C laid out flat. The disposable wearable absorbent article 100C includes a front waist edge 102 and a back waist edge 104, along with a front 101 and a back 105, which are separated by a lateral centerline 116.

In FIG. 1C, a longitudinal centerline 113 and the lateral centerline 116 provide lines of reference for referring to relative locations of the disposable wearable absorbent article 100C. The longitudinal centerline 113 and the lateral centerline 116 cross at a center 119 of the disposable wearable absorbent article 100C. When a first location is nearer to the longitudinal centerline 113 than a second location, the first location can be considered laterally inboard 112 to the second location. Similarly, the second location can be considered laterally outboard 111 from the first location. When a third location is nearer to the lateral centerline 116 than a fourth location, the third location can be considered longitudinally inboard 115 to the fourth location. Also, the fourth location can be considered longitudinally outboard 114 from the third location.

FIG. 1C includes arrows indicating relative directions for laterally outboard 111, laterally inboard 112, longitudinally outboard 114, and longitudinally inboard 115, each with respect to the disposable wearable absorbent article 100C. Throughout the present disclosure, a reference to a longitudinal dimension, measurement, line, or direction refers to a dimension, measurement, line, or direction that is substantially or completely parallel to the longitudinal centerline 113 and a reference to a lateral dimension, measurement, line, or direction refers to a dimension, measurement, line, or direction that is substantially or completely parallel to the lateral centerline 116. The terminology for describing relative locations, as discussed above, is used for disposable wearable absorbent articles throughout the present disclosure. This terminology can also be similarly applied to various other absorbent articles, as will be understood by one of ordinary skill in the art.

The disposable wearable absorbent article 100C includes a topsheet 106, an outer cover 109, an acquisition layer 191, a distribution layer 193, and an absorbent core 195. A portion of the outer cover 109 is shown as broken to illustrate a portion of the topsheet 106 and a portion of the absorbent core 195. A portion of the absorbent core 195 is shown as broken to illustrate a portion of the distribution layer 193. A portion of the distribution layer 193 is shown as broken to illustrate a portion of the acquisition layer 191.

The disposable wearable absorbent article 100C includes a number of visual fullness indicators in various exemplary locations and orientations. The disposable wearable absorbent article 100C includes a longitudinally oriented visual fullness indicator 141 configured for a male wearer and a longitudinally oriented visual fullness indicator 151 configured for a female wearer, both disposed along the longitudinal centerline 113 in the front 101. The disposable wearable absorbent article 100C also includes a longitudinally oriented visual fullness indicator 145 configured for a male wearer and a longitudinally oriented visual fullness indicator 155 configured for a female wearer, both disposed along the longitudinal centerline 113 in the back 105.

In the disposable wearable absorbent article 100C, the visual fullness indicators are oriented substantially radially out from the center 119. However, in addition to the locations and orientations illustrated in FIG. 1C, a visual fullness indicator of the present disclosure can be disposed in various alternate locations and orientations in an absorbent article, as will be understood by one of ordinary skill in the art. As an example, a visual fullness indicator can be disposed in a pant-type disposable wearable absorbent article in a lateral orientation or at an angle with respect to a centerline of the article.

Figure 2A:
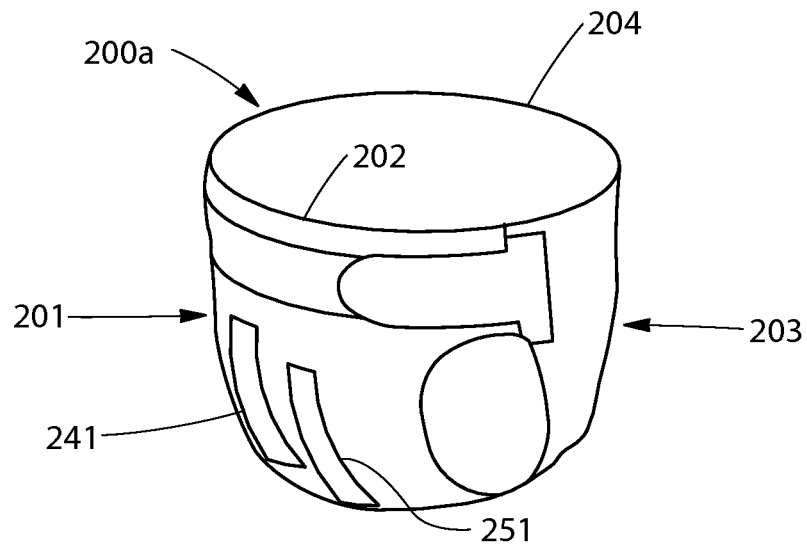
FIG. 2A illustrates a front-fastenable disposable wearable absorbent article with gender specific visual wetness indicators in the front, according to embodiments of the present disclosure.

FIG. 2A illustrates an outside perspective view of a front 201 and a side 203 of a front-fastenable disposable wearable absorbent article 200A formed for wearing. The front-fastenable disposable wearable absorbent article 200A includes a waist opening 207 and a leg opening 208. The absorbent article 200A includes a front waist edge 202 and a back waist edge 204. The absorbent article 200A also includes a longitudinally oriented visual fullness indicator 241 configured for a male wearer and a longitudinally oriented visual fullness indicator 251 configured for a female wearer, both disposed in the front 201.

While the present disclosure refers to front-fastenable absorbent articles, the present disclosure also contemplates alternate embodiments of absorbent articles having gender specific wetness indicating, as described herein, wherein the absorbent articles are rear-fastenable. Thus, each embodiment of an absorbent article of the present disclosure that is described as front-fastenable can also be configured to be rear fastenable, as will be understood by one of ordinary skill in the art.

Figure 2B:
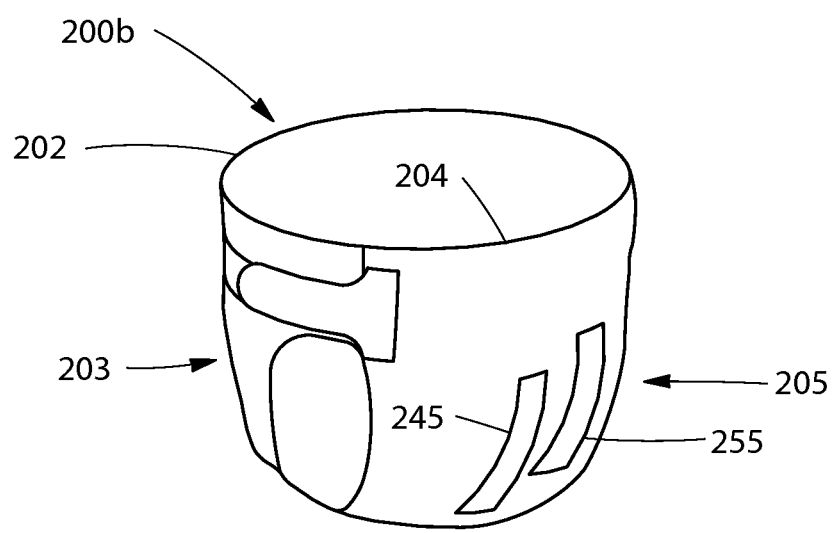
FIG. 2B illustrates a front-fastenable disposable wearable absorbent article with gender specific visual wetness indicators in the back, according to embodiments of the present disclosure.

FIG. 2B illustrates an outside perspective view of a side 203 and a back 205 of a front-fastenable disposable wearable absorbent article 200B formed for wearing. The front-fastenable disposable wearable absorbent article 200B includes a waist opening 207 and a leg opening 208. The absorbent article 200B includes a front waist edge 202 and a back waist edge 204. The absorbent article 200B also includes a longitudinally oriented visual fullness indicator 245 configured for a male wearer and a longitudinally oriented visual fullness indicator 255 configured for a female wearer, both disposed in the back 205.

Figure 2C:
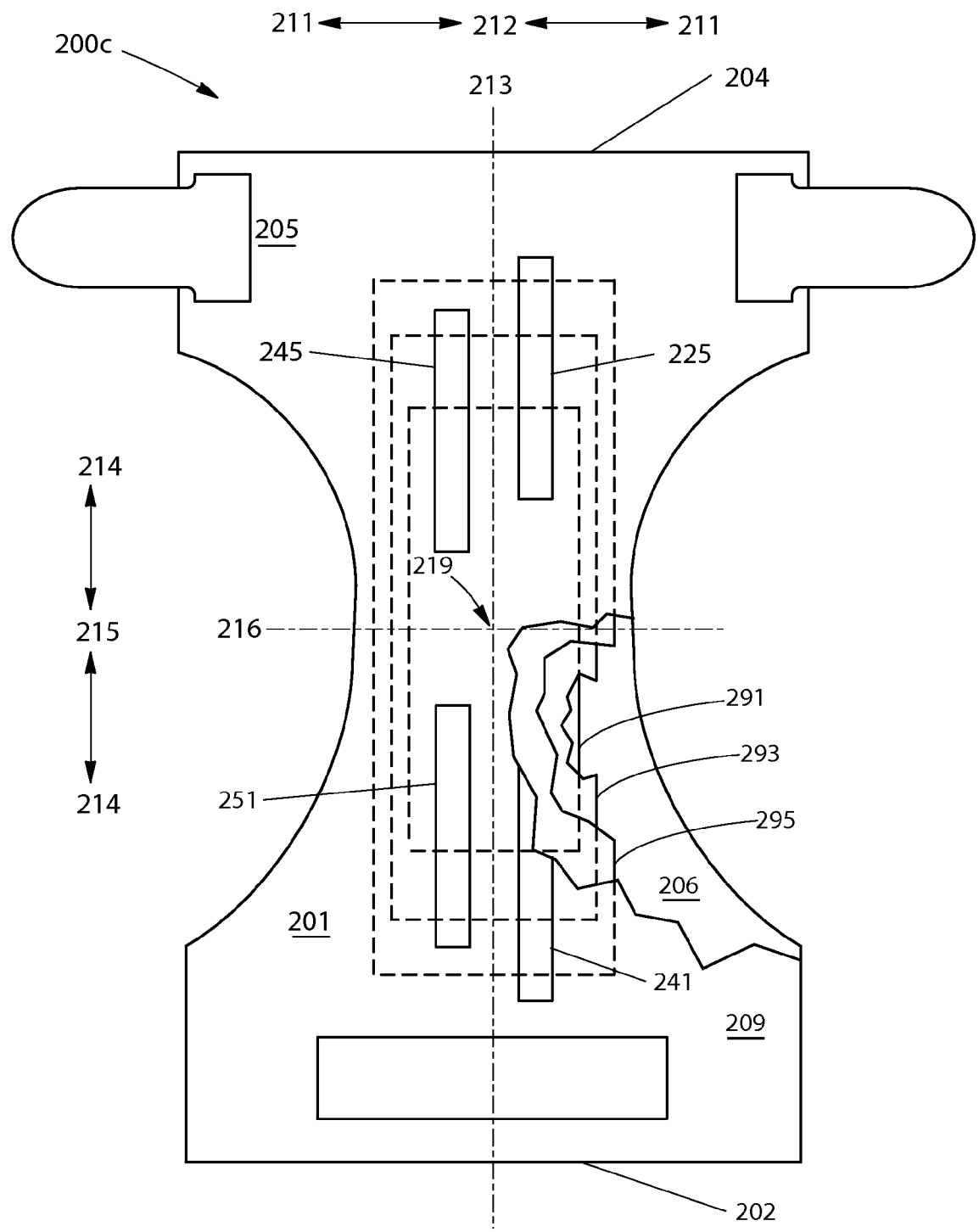
FIG. 2C illustrates a front-fastenable disposable wearable absorbent article with a number of gender specific visual wetness indicators, according to embodiments of the present disclosure.

FIG. 2C illustrates an outside plan view of a front-fastenable disposable wearable absorbent article 200C laid out flat. The disposable wearable absorbent article 200C includes a front 201, a front waist edge 202, a back waist edge 204, a back 205, a longitudinal centerline 213, and a lateral centerline 216.

The disposable wearable absorbent article 200C includes a topsheet 206, an outer cover 209, an acquisition layer 291, a distribution layer 293, and an absorbent core 295. A portion of the outer cover 209 is shown as broken to illustrate a portion of the topsheet 206 and a portion of the absorbent core 295. A portion of the absorbent core 295 is shown as broken to illustrate a portion of the distribution layer 293. A portion of the distribution layer 293 is shown as broken to illustrate a portion of the acquisition layer 291.

The disposable wearable absorbent article 200C includes a number of visual fullness indicators in various exemplary locations and orientations. The disposable wearable absorbent article 200C includes a longitudinally oriented visual fullness indicator 241 configured for a male wearer and a longitudinally oriented visual fullness indicator 251 configured for a female wearer, both disposed along the longitudinal centerline 213 in the front 201. The disposable wearable absorbent article 200C also includes a longitudinally oriented visual fullness indicator 245 configured for a male wearer and a longitudinally oriented visual fullness indicator 255 configured for a female wearer, both disposed along the longitudinal centerline 213 in the back 205.

In the disposable wearable absorbent article 200C, the visual fullness indicators are oriented substantially radially out from the center 219. However, in addition to the locations and orientations illustrated in FIG. 2C, a visual fullness indicator of the present disclosure can be disposed in various alternate locations and orientations in an absorbent article, as will be understood by one of ordinary skill in the art. As an example, a visual fullness indicator can be disposed in a pant-type disposable wearable absorbent article in a lateral orientation or at an angle with respect to a centerline of the article.

Figure 3:
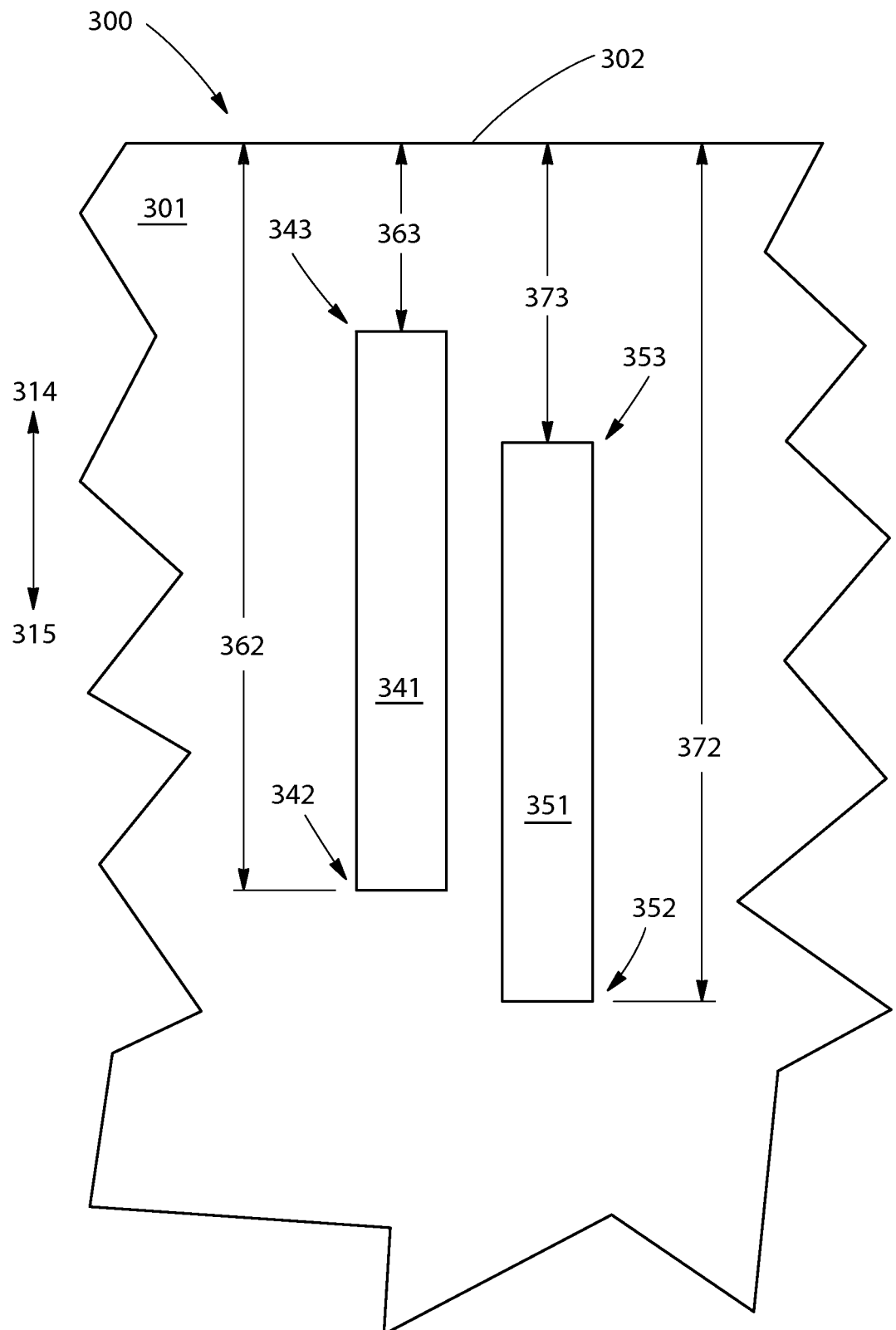
FIG. 3 illustrates a portion of a front of an absorbent article with a visual wetness indicator configured for a male wearer and a visual wetness indicator configured for a female wearer, according to embodiments of the present disclosure.

FIG. 3 illustrates an outside plan view of a portion of a front 301 of an absorbent article 300 laid out flat. In various embodiments, the absorbent article 300 can be a disposable wearable absorbent article, such as a pant-type disposable wearable absorbent article or a front-fastenable disposable wearable absorbent article. In FIG. 3, the portion of the front 301 is bounded by a front waist edge 302 of the absorbent article 300 and by broken lines, since the portion is illustrated as separate from the rest of the absorbent article 300. For reference, FIG. 3 illustrates arrows indicating relative directions for longitudinally outboard 314 and longitudinally inboard 315 for the absorbent article 300.

The portion of the front 301 of the absorbent article 300 includes a wetness indicator 341 and a wetness indicator 351. The wetness indicator 341 is a male visual fullness indicator, configured for a male wearer. The wetness indicator 351 is a female visual fullness indicator, configured for a female wearer. However, in various embodiments the wetness indicator 341 and/or the wetness indicator 351 can be configured as another form of visual wetness indicator, as will be understood by one of skill in the art.

The male visual fullness indicator 341 and the female visual fullness indicator 351 are each disposed offset from a center of the absorbent article 300. In various embodiments, one or more parts of a visual fullness indicator can be disposed near, at, or overlapping a center of an absorbent article. For example, a single indicating area can extend from a front of an absorbent article, through the center of the absorbent article, to the back of the absorbent article. In such an embodiment, a farthest inboard point along the indicating area can be considered an inboard end of two indicators.

The male visual fullness indicator 341 and the female visual fullness indicator 351 each include one visual fullness indicating area. The male visual fullness indicator 341 includes a longitudinally inboard end 342 and a longitudinally outboard end 343, while the female visual fullness indicator 351 includes an inboard end 352 and an outboard end 353. The male visual fullness indicator 341 has an overall indicator length, measured along the male visual fullness indicator 341 from the inboard end 342 to the outboard end 343. The female visual fullness indicator 351 has an overall indicator length, measured along the female visual fullness indicator 351 from the inboard end 352 to the outboard end 353. The male visual fullness indicator 341 and the female visual fullness indicator 351 each has an overall shape that is substantially elongated and each has a substantially uniform width along its entire overall indicator length.

In some embodiments a visual fullness indicator can have an overall shape that is more or less elongated. In various embodiments, part, or parts, or all of a visual fullness indicator can be straight, curved, angled, segmented, or any regular or irregular geometric shape (such as a square, rectangle, triangle, trapezoid, octagon, hexagon, star, half circle, a quarter circle, a half oval, a quarter oval, a radial pattern, etc.), a recognizable image (such as a letter, number, word, character, face of an animal, face of a person, etc.), or another recognizable image (such as a plant, a car, etc.), another shape, or combinations of any of these shapes. In some embodiments, a visual fullness indicator can have varying widths over part, or parts, or all of its length. Further, a visual fullness indicating area can also be configured in any of these ways.

A visual fullness indicator is a visually distinct and recognizable pathway of one or more visual indicators and/or visual indicating areas. A pathway is recognizable in its visual context. In other words, a pathway is distinct and recognizable, when compared with the appearance of a surrounding area.

The pathway of a visual fullness indicator has two defined ends, a middle between the two ends, and a defined length from its one end to its other end. A visual fullness indicator can have one or more widths, each of which is less than its defined length.

A visual fullness indicator can be configured in various forms. For example, a visual fullness indicator can be formed by a single, continuous indicating area disposed along a pathway. As another example, a visual fullness indicator can be formed by a plurality of discrete indicators and/or discrete indicating areas disposed along a pathway.

The male visual fullness indicator 341 and the female visual fullness indicator 351 are each in fluid communication with an absorbent core of the absorbent article 300 along their entire overall indicator length. In various embodiments, a visual indicator can be configured such that part, or parts, or substantially all, or all of the indicator is in fluid communication with an absorbent core. In some embodiments, a visual indicator can be configured such that part, or parts, or substantially all, or all of the indicator overlaps an absorbent core or such that part, or parts, or substantially all, or all of the indicator does not overlap an absorbent core.

Throughout the present disclosure, fluid communication refers to a configured structural relationship that allows a liquid substance to freely pass from one element or location to another element or location; however, one element or location is not necessarily considered to be in fluid communication with another element or location merely by being connected or joined to a common element through which liquid can possibly pass. This definition of fluid communication is further explained by the following examples.

For example, if one element is configured to be in direct physical contact with another element such that a liquid substance can freely pass from the one element through the contacting portions to the other element, then the elements can be considered to be in fluid communication. As another example, if one element is connected to another element by a means for fluid communication such that a liquid substance can freely pass from the one element through the means for fluid communication to the other element, then the elements can be considered to be in fluid communication.

As a further example, if one element is connected to a substrate and another element is connected to the same substrate, but the substrate does not allow a liquid substance to freely pass through, then the elements are considered to be out of fluid communication. This holds true even if liquid can possibly pass through the substrate, so long as the liquid cannot pass through freely. The above definition of fluid communication, as explained through these examples, will be understood by one of ordinary skill in the art.

Throughout the present disclosure, the term liquid bodily exudate refers to any bodily substances exuded in liquid form (e.g. urine) and/or any liquid-like bodily substances (e.g. runny feces).

In various embodiments, part, or parts, or all of a visual fullness indicating area can be configured to change from one or more initial visual states to one or more subsequent visual states. Also, in some embodiments of the present disclosure, for a particular portion of a visual fullness indicating area, an initial visual state and a subsequent visual can each be any visual state, so long as the subsequent visual state is visually distinguishable from the first initial visual state.

Throughout the present disclosure, the term visual state refers to an appearance which can be perceived by an unaided human with normal vision in standard lighting conditions. A visual state can comprise one or more colors, variations of color(s), patterns, letters, numbers, symbols, designs, images, and/or other visual devices. Colors include well known colors such as red, orange, yellow, green, blue, purple, etc. Variations of a color include variations in chroma, hue, and brightness, among others. While these informal terms are used for ease of reference, embodiments of the present disclosure are intended to encompass all colors which can be perceived by an unaided human with normal vision in standard lighting conditions.

Throughout the present disclosure, visual states are considered visually distinguishable if they can be recognized as different on sight by an unaided human with normal vision in standard lighting conditions. As an example, an unaided human with normal vision in standard lighting conditions should be able to recognize blue and yellow as different colors on sight. Thus, the blue and the yellow would be considered visually distinguishable visual states. As another example, an unaided human with normal vision in standard lighting conditions may be able to recognize a light shade of orange and a dark shade of orange as different shades of a color on sight. Thus, the light shade of orange and the dark shade of orange would be considered visually distinguishable visual states. As a further example, an unaided human with normal vision in standard lighting conditions may be able to recognize a first pattern and a second pattern as different visual states on sight. Thus, the first pattern and the second pattern would be considered visually distinguishable visual states.

As a still further example, an unaided human with normal vision in standard lighting conditions should be able to recognize an area with letters and a blank area as different visual states on sight. Thus, the area with letters and the blank area would be considered visually distinguishable visual states. Similarly, an area with numbers, symbols, designs, images, and/or other visual devices would also be considered visually distinguishable from a blank area or from a uniformly colored area. In addition to these examples, there are many other possible visually distinguishable visual states, as will be understood by one or ordinary skill in the art.

There are several ways by which absorbent articles of the present disclosure can be configured to include indicating areas that change visual states when indicating the presence of a bodily exudate, as will be understood by one of ordinary skill in the art. For example, an absorbent article can be configured to include such visual fullness indicators as described in the following U.S. patents: U.S. Pat. No. 4,022,211, entitled "Wetness indicator for absorbent pads" issued on May 10, 1977 to Timmons, et al.; U.S. Pat. No. 4,231,370, entitled "Disposable diaper type garment having wetness indicator" issued on Nov. 4, 1980 to Mroz, et al.; U.S. Pat. No. 4,327,731, entitled "Moisture indicator" issued on May 4, 1982 to Powell; U.S. Pat. No. 4,681,576, entitled "Wetness indicating hot-melt adhesive" issued on Jul. 21, 1987 to Colon, et al.; U.S. Pat. No. 4,705,513, entitled "Disposable diaper with wetness indicator" issued on Nov. 10, 1987 to Sheldon, et al.; U.S. Pat. No. 4,738,674, entitled "Moisture indicator apparatus and method" issued on Apr. 19, 1988 to Todd, et al.; U.S. Pat. No. 4,743,238, entitled "Wetness indicating hot-melt adhesive" issued on May 10, 1988 to Colon et al.; U.S. Pat. No. 4,895,567, entitled "Wetness indicating hot-melt adhesive" issued on Jan. 23, 1990 to Colon et al.; U.S. Pat. No. 4,931,051, entitled "Wetness indicator" issued on Jun. 5, 1990 to Castello; U.S. Pat. No. 5,035,691, entitled "Hot melt moisture indicator material for disposable articles" issued on Jul. 30, 1991 to Ziminel, et al.; U.S. Pat. No. 5,066,711, entitled "Wetness indicating hot-melt adhesive" issued on Nov. 19, 1991 to Colon et al.; U.S. Pat. No. 5,089,548, entitled "Hot melt moisture indicator material for disposable articles" issued on Feb. 18, 1992 to Zimmel, et al.; U.S. Pat. No. 5,167,652, entitled "Moisture sensitive film" issued on Dec. 1, 1992 to Mueller; U.S. Pat. No. 5,342,861, entitled "Hot melt wetness indicator" issued on Aug. 30, 1994 to Raykovitz; U.S. Pat. No. 5,354,289 entitled "Absorbent product including super absorbent material and fluid absorption capacity monitor" issued on Oct. 11, 1994 to Mitchell, et al.; entitled "Capacity indicia for absorbent articles" issued on Nov. 1, 1994 to Osborne, et al.; U.S. Pat. No. 5,647,863, entitled "Absorbent article with clean appearance and capacity signal means" issued on Jul. 15, 1997 to Hammons, et al.; U.S. Pat. No. 5,690,624, entitled "Disposable diaper" issued on Nov. 25, 1997 to Sasaki, et al.; U.S. Pat. No. 5,766,212, entitled "Disposable diaper" issued on Jun. 16, 1998 to Jitoe, et al.; U.S. Pat. No. 6,075,178, entitled "Absorbent article with wetness indicator" issued on Jun. 13, 2000; U.S. Pat. No. 6,515,194, entitled "Diaper having centrally-located chromatographic layer with peripherally-located wetness indicator" issued on Feb. 4, 2003 to Neading, et al.; U.S. Pat. No. 6,596,918, entitled "Absorbent articles having wetness indicating graphics and employing masking techniques" issued on Jul. 22, 2003 to Wehrle, et al.; U.S. Pat. No. 6,653,522, entitled "Hot melt adhesives based on sulfonated polyesters comprising wetness indicator" issued on Nov. 25, 2003 to Blumenthal, et al.; U.S. Pat. No. 6,772,708, entitled "Wetness indicator having improved colorant retention" issued on Aug. 10, 1994 to Klofta, et al.; U.S. Pat. No. 6,904,865, entitled "Wetness indicator having improved colorant retention and durability" issued on Jun. 14, 2005 to Klofta, et al.; U.S. Pat. No. 7,159,532, entitled "Wetness indicator having improved colorant retention and durability" issued on Jan. 9, 2007 to Klofta, et al.; U.S. Pat. No. 7,172,667, entitled "System and method for incorporating graphics into absorbent articles" issued on Feb. 6, 2007 to Vergona; U.S. Pat. No. 7,178,571, entitled "System and method for incorporating graphics into absorbent articles" issued on Feb. 20, 2007 to Vergona; U.S. Pat. No. 7,306,764, entitled "Wetness indicator" issued on Dec. 11, 2007 to Mody; and U.S. Pat. No. 7,332,642, entitled "Disposable absorbent articles having printed wetness indicators" issued on Feb. 19, 2008 to Liu, each of which is incorporated herein by reference.

In the embodiment of FIG. 3, the male visual fullness indicator 341 and the female visual fullness indicator 351 are each configured to change from one or more initial visual states to one or more subsequent visual states when indicating the presence of a liquid bodily exudate.

An absorbent article can be configured such that part, or parts, or all of a visual indicating area is visible from outside of the absorbent article when the absorbent article is worn by a wearer. For example, a visual fullness indicating area can be visible when viewing an outside of an outer cover of an absorbent article. As a result, at least some of a subsequent visual state of the visual indicating area will be visible from outside of the absorbent article.

The absorbent article 300 can be configured such that part, or parts, or all of each of the male visual fullness indicator 341 and the female visual fullness indicator 351 are visible from outside of the absorbent article 300 when the absorbent article 300 is worn by a wearer. As a result, at least some of the subsequent visual state(s) will be visible from outside of the absorbent article 300.

The male visual fullness indicator 341 and the female visual fullness indicator 351 can each indicate the presence of a liquid bodily exudate by a wet edge that continuously moves along the visual fullness indicator from the inboard end to the outboard end such that the visual fullness indicator progressively changes from an initial visual state to a subsequent visual state along its length. The partial or complete absence or presence of a subsequent visual state on a visual fullness indicator can indicate the fullness of an absorbent article. For instance, the presence of a subsequent visual state in an inboard portion of a visual fullness indicator can indicate that an absorbent article is somewhat filled, the presence of a subsequent visual state in a longitudinally intermediate portion of a visual fullness indicator can indicate that an absorbent article is approaching full, and the presence of a subsequent visual state in an outboard portion of a visual fullness indicator can indicate that an absorbent article is full.

The male visual fullness indicator 341 and the female visual fullness indicator 351 can help provide certainty about the fullness of the absorbent article 300 for a wearer of a particular gender. The male visual fullness indicator 341 can be configured to visually indicate the male gender. The female visual fullness indicator 351 can be configured to visually indicate the female gender.

An indicator can be configured to visually indicate a particular gender by comprising one or more colors, variations of color(s), patterns, letters, numbers, symbol, designs, images, and/or other visual devices, associated with the gender in the initial visual state of the indicator and/or in the subsequent visual state of the indicator and/or in indicia for the indicator or in graphics associated with the indicator. As examples, a male indicator be associated with the color blue, a variation of the color blue, the color green, a variation of the color green, a Mars symbol (i.e. a circle with a protruding arrow (representing the shield and spear of the Roman god Mars), such as Unicode entry U+2642, which is ♂), an image of a person of male gender, the letter B, the letter M, the word BOY, the word MALE, the word MAN, any other word (from this language or another language) associated with the male gender, or a similar visual device, or combinations of any of these. Also as examples, a female indicium can be associated with the color pink, a variation of the color pink, the color purple, a variation of the color purple, a Venus symbol (i.e. a circle with an cross underneath (representing the hand mirror and comb of the Roman goddess Venus) such as Unicode entry U+2640, which is ♀), an image of a person of female gender, the letter G, the letter F, the letter W, the word GIRL, the word FEMALE, the word WOMAN, any other word (from this language or another language) associated with the female gender, or a similar visual device, or combinations of any of these. Further, a seemingly arbitrary color, pattern, letter, number, symbol, design, image, or other visual device may be intentionally associated with a particular gender and thus used as a male or female indicium.

While the portion of the front 301 of the absorbent article 300 includes one male visual fullness indicator 341 and one female visual fullness indicator 351, an absorbent article can include various numbers of wetness indicators. For example, an absorbent article can be configured to include one or two or three or more male indicators and/or one or two or three or more female indicators. In an alternate embodiment, an absorbent article can be configured to include one or more gender specific indicator for only one particular gender.

Each of the gender specific indicators 341 and 351 is configured such that the progressive presence of the subsequent visual state in the visual fullness indicator indicates varying degrees of fullness in the absorbent article 300 for a wearer of a particular gender. The male visual fullness indicator 341 is configured to indicate varying degrees of fullness in the absorbent article 300 for liquid bodily exudates received from a wearer of the male gender. Similarly, the female visual fullness indicator 351 is configured to indicate degrees of fullness in the absorbent article 300 for liquid bodily exudates received from a wearer of the female gender.

In the embodiment of FIG. 3, a visual state change at the inboard end 342 of the male visual fullness indicator 341 indicates the same degree of fullness in the absorbent article 300 as indicated by a visual state change at the inboard end 352 of the female visual fullness indicator 351. Also, a visual state change in the longitudinally central portion of the male visual fullness indicator 341 indicates the same degree of fullness in the absorbent article 300 as indicated by a visual state change in the longitudinally central portion of the female visual fullness indicator 351. Further, a visual state change at the outboard end 343 of the male visual fullness indicator 341 indicates the same degree of fullness in the absorbent article 300 as indicated by a visual state change at the outboard end 353 of the female visual fullness indicator 351. However, this correspondence is not required, and in some embodiments may not be present.

In the embodiment of FIG. 3, the male visual fullness indicator 341 and the female visual fullness indicator 351 are disposed proximate to each other. However, in various embodiments, gender specific indicators can be disposed remote from each other.

In the embodiment of FIG. 3, the male visual fullness indicator 341 has an overall indicator length that is the same as an overall indicator length of the female visual fullness indicator 351. However, in various embodiments gender specific indicators can have differing overall lengths.

The gender specific indicators 341 and 351 can be positioned in the absorbent article 300 to account for a wearer's gender. In particular, the male visual fullness indicator 341 can be disposed in the absorbent article 300 to account for the location of the male pee point, which is positioned toward the front of the crotch on the male anatomy. As a result, when a male wearer urinates into a disposable wearable absorbent article, the urine will be initially received into a front portion of the article. In order to account for this front-loading of urine from a male, an absorbent article can include a male wetness indicator disposed relatively closer to the front of the article, when compared with a female wetness indicator.

Similarly, the female visual fullness indicator 351 can be disposed in the absorbent article 300 to account for the location of the female pee point, which is positioned toward the middle of the crotch on the female anatomy. As a result, when a female wearer urinates into a disposable wearable absorbent article, the urine will be initially received into a longitudinally central portion of the article. In order to account for this central-loading of urine from a female, an absorbent article can include a female wetness indicator disposed relatively farther from the front of the article, when compared with a male wetness indicator. The present disclosure contemplates that, for some infants, the difference between male and female pee points results in a urine-loading difference of about 2 centimeters, measured longitudinally in a disposable wearable absorbent article.

This difference in relative disposition, for the male visual fullness indicator 341 and the female visual fullness indicator 351, can be understood in a number of different ways. In the front 301 of the absorbent article 300, the inboard end 342 of the male visual fullness indicator 341 can be disposed at a longitudinal distance 362 from the front edge 302. The inboard end 352 of the female visual fullness indicator 351 can be disposed at a longitudinal distance 372 from the front edge 302. The longitudinal distance 372 is greater than the longitudinal distance 362. That is, the inboard end 342 of the male visual fullness indicator 341 is closer to the front edge 302 than the inboard end 352 of the female visual fullness indicator 351. Also in the front 301 of the absorbent article 300, the outboard end 343 of the male visual fullness indicator 341 can be disposed at a longitudinal distance 363 from the front edge 302. The outboard end 353 of the female visual fullness indicator 351 can be disposed at a longitudinal distance 373 from the front edge 302. The longitudinal distance 373 is greater than the longitudinal distance 363. That is, the outboard end 343 of the male visual fullness indicator 341 is closer to the front edge 302 than the outboard end 353 of the female visual fullness indicator 351. Any of these relative dispositions for a male visual fullness indicator and a female visual fullness indicator can apply to all of the embodiments of the present disclosure.

In the embodiment of FIG. 3, the male visual fullness indicator 341 and the female visual fullness indicator 351 are relatively disposed in the absorbent article 300, as described above, to account for differences between the male and female anatomy. The male visual fullness indicator 341 and the female visual fullness indicator 351 can be easily understood as providing gender specific wetness indicating.

An absorbent article with gender specific wetness indicating can help provide certainty about the fullness of the absorbent article for a wearer of a particular gender. By knowing how full an article is, the article can be changed after the wearer has appropriately utilized the capacity of the article. Also, by knowing how full an article is, the article can be changed before it is likely to leak.

One of ordinary skill in the art can select an appropriate particular location and orientation as well as specific dimensions and other physical characteristics for visual fullness indicators of the present disclosure in order for an indicator to provide visual state change signals that indicate the degree of fullness, the remaining capacity, and/or the leakage risk for a particular absorbent article. In various embodiments, the absorbent article can also include indicia correlating the visual state change signals with fullness, capacity, and/or leakage risk. Further, in some embodiments, instructions for the absorbent article can explain the correlation between the visual state change signals, the indicia, and fullness, capacity, and/or leakage risk. For example, such instructions can be provided on packaging for the absorbent article or on printed material accompanying the absorbent article. Still further, the correlation between the visual state change signals, the indicia, and fullness, capacity, and/or leakage risk can be communicated through various advertising media.

Figure 4:
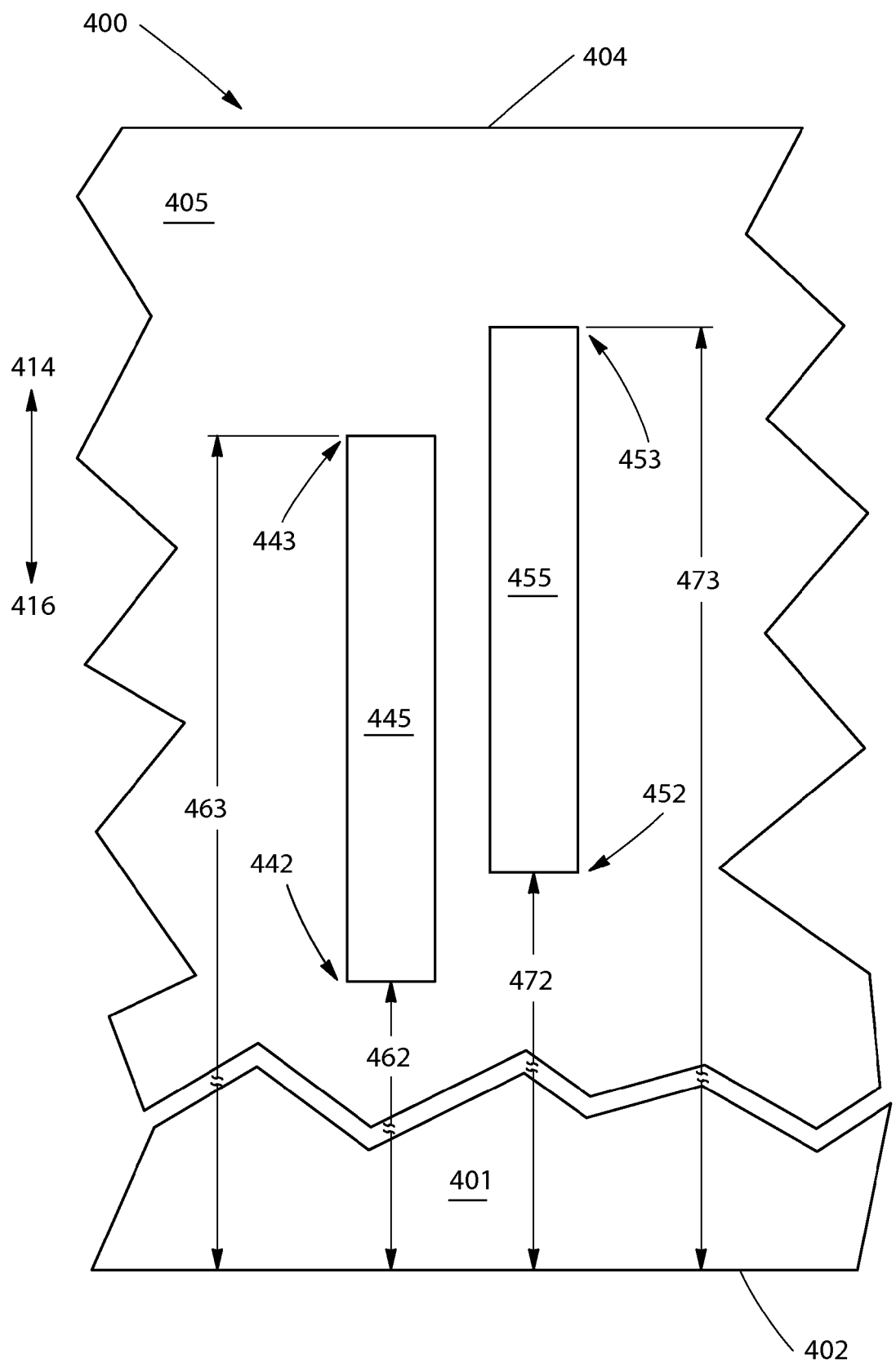
FIG. 4 illustrates a portion of a back of an absorbent article with a visual wetness indicator configured for a male wearer and a visual wetness indicator configured for a female wearer, according to embodiments of the present disclosure.

FIG. 4 illustrates an outside plan view of a portion of a back 405 of an absorbent article 400 laid out flat. In various embodiments, the absorbent article 400 can be a disposable wearable absorbent article, such as a pant-type disposable wearable absorbent article or a front-fastenable disposable wearable absorbent article. In FIG. 4, the portion of the front 405 is bounded by a back waist edge 404 of the absorbent article 400 and by broken lines, since the portion is illustrated as separate from the rest of the absorbent article 400. FIG. 4 also illustrates a portion of a front 401 of the absorbent article 400, including a front waist edge 402. For reference, FIG. 4 illustrates arrows indicating relative directions for longitudinally outboard 414 and longitudinally inboard 415 for the absorbent article 400.

The portion of the back 405 of the absorbent article 400 includes a wetness indicator 445 and a wetness indicator 455. The wetness indicator 445 is a male visual fullness indicator, configured for a male wearer. The wetness indicator 455 is a female visual fullness indicator, configured for a female wearer. However, in various embodiments the wetness indicator 445 and/or the wetness indicator 455 can be configured as another form of visual wetness indicator, as will be understood by one of skill in the art.

The male visual fullness indicator 445 and the female visual fullness indicator 455 are each disposed offset from a center of the absorbent article 400. The male visual fullness indicator 445 and the female visual fullness indicator 455 each include one visual fullness indicating area. The male visual fullness indicator 445 includes a longitudinally inboard end 442 and a longitudinally outboard end 443, while the female visual fullness indicator 455 includes an inboard end 452 and an outboard end 453. The male visual fullness indicator 445 has an overall indicator length, measured along the male visual fullness indicator 445 from the inboard end 442 to the outboard end 443. The female visual fullness indicator 455 has an overall indicator length, measured along the female visual fullness indicator 455 from the inboard end 452 to the outboard end 453. The male visual fullness indicator 445 and the female visual fullness indicator 455 each has an overall shape that is substantially elongated and each has a substantially uniform width along its entire overall indicator length.

The male visual fullness indicator 445 and the female visual fullness indicator 455 are each configured to change from one or more initial visual states to one or more subsequent visual states when indicating the presence of a liquid bodily exudate. The absorbent article 400 can be configured such that part, or parts, or all of each of the male visual fullness indicator 445 and the female visual fullness indicator 455 are visible from outside of the absorbent article 400 when the absorbent article 400 is worn by a wearer. As a result, at least some of the subsequent visual state(s) will be visible from outside of the absorbent article 400.

The male visual fullness indicator 445 and the female visual fullness indicator 455 can each indicate the presence of a liquid bodily exudate by a wet edge that continuously moves along the visual fullness indicator from the inboard end to the outboard end such that the visual fullness indicator progressively changes from an initial visual state to a subsequent visual state along its length.

The male visual fullness indicator 445 and the female visual fullness indicator 455 can help provide certainty about the fullness of the absorbent article 300 for a wearer of a particular gender. The male visual fullness indicator 445 and the female visual fullness indicator 455 in the embodiment of FIG. 4 are configured in the same manner as, respectively, the male visual fullness indicator 341 and the female visual fullness indicator 351 in the embodiment of FIG. 3, except as described below.

The embodiment of FIG. 4 differs from the embodiment of FIG. 3 in that FIG. 3 illustrates gender specific visual fullness indicators in a portion of a front 301 of an absorbent article while FIG. 4 illustrates gender specific visual fullness indicators in a portion of a back 405 of an absorbent article. The gender specific visual fullness indicators 445 and 455 of the embodiment of FIG. 4 can still be positioned in the absorbent article 400 to account for a wearer's gender. The male visual fullness indicator 445 can still be disposed in the absorbent article 400 to account for the front location of the male pee point, and the female visual fullness indicator 455 can still be disposed in the absorbent article 400 to account for the central location of the female pee point. The gender specific indicators 445 and 455 still have the same relative disposition with respect to the front edge 402 of the absorbent article. However, the relative disposition of the gender specific indicators appears different in the back 405 than in a front. The result of this front/back difference is that, in the front the male visual fullness indicator is disposed relatively outboard with respect to the female visual fullness indicator, while in the back the male visual fullness indicator is disposed relatively inboard with respect to the female visual fullness indicator, as described below.

This difference in relative disposition, for the male visual fullness indicator 445 and the female visual fullness indicator 455, can be understood in a number of different ways. In the back 405 of the absorbent article 400, the inboard end 442 of the male visual fullness indicator 445 can be disposed at a longitudinal distance 462 from the front edge 402. The inboard end 452 of the female visual fullness indicator 451 can be disposed at a longitudinal distance 472 from the front edge 402. The longitudinal distance 472 is greater than the longitudinal distance 462. That is, the inboard end 442 of the male visual fullness indicator 445 is closer to the front edge 402 than the inboard end 452 of the female visual fullness indicator 455. Also in the back 405 of the absorbent article 400, the outboard end 443 of the male visual fullness indicator 445 can be disposed at a longitudinal distance 463 from the front edge 402. The outboard end 453 of the female visual fullness indicator 455 can be disposed at a longitudinal distance 473 from the front edge 402. The longitudinal distance 473 is greater than the longitudinal distance 463. That is, the outboard end 443 of the male visual fullness indicator 445 is closer to the front edge 402 than the outboard end 453 of the female visual fullness indicator 455. Any of these relative dispositions for a male visual fullness indicator and a female visual fullness indicator can apply to all of the embodiments of the present disclosure.

In the embodiment of FIG. 4, the male visual fullness indicator 445 and the female visual fullness indicator 455 are relatively disposed in the absorbent article 400, as described above, to account for differences between the male and female anatomy. The male visual fullness indicator 445 and the female visual fullness indicator 455 can be easily understood as providing gender specific wetness indicating.

An absorbent article with gender specific wetness indicating can help provide certainty about the fullness of the absorbent article for a wearer of a particular gender. By knowing how full an article is, the article can be changed after the wearer has appropriately utilized the capacity of the article. Also, by knowing how full an article is, the article can be changed before it is likely to leak.

Further, the present disclosure contemplates that an absorbent article, such as a disposable wearable absorbent article, can have one or more visual fullness indicators configured as described herein and further configured with various additional and/or alternate structures and/or functions as described below.

One or more embodiments of the present disclosure can be combined with one or more embodiments of U.S. non-provisional patent application Ser. No. 12/346,481 entitled "Absorbent Articles with Multiple Indicating Widths," filed on Dec. 30, 2008 and/or U.S. non-provisional patent application entitled "Absorbent Articles with Multiple Indicating Widths," filed on Dec. 23, 2009 under Ser. No. 12/646,315, each of which is incorporated herein by reference. A disposable wearable absorbent article with gender specific indicating can also have multiple indicating widths.

One or more embodiments of the present disclosure can be combined with one or more embodiments of U.S. non-provisional patent application Ser. No. 12/346,496 entitled "Disposable Wearable Absorbent Articles with Gender Specific Indicia," filed on Dec. 30, 2008 and/or U.S. non-provisional patent application entitled "Disposable Wearable Absorbent Articles with Gender Specific Indicia," filed on Dec. 23, 2009 under Ser. No. 12/646,334, Reach of which is incorporated herein by reference. A disposable wearable absorbent article with gender specific indicating can also have gender specific indicia.

One or more embodiments of the present disclosure can be combined with one or more embodiments of U.S. non-provisional patent application Ser. No. 12/346,520 entitled "Absorbent Articles with Patterns of Indicating," filed on Dec. 30, 2008 and/or U.S. non-provisional patent application entitled "Absorbent Articles with Patterns of Indicating," filed on Dec. 23, 2009 under Ser. No. 12/646,393, each of which is incorporated herein by reference. A disposable wearable absorbent article with gender specific indicating can also have patterns of indicating.

One or more embodiments of the present disclosure can be combined with one or more embodiments of U.S. provisional patent application 61/141,573 entitled "Absorbent Articles with Primary and Secondary Indicating," filed on Dec. 30, 2008 and/or U.S. non-provisional patent application entitled "Absorbent Articles with Primary and Secondary Indicating," filed on Dec. 23, 2009 under Ser. No. 12/646,414, each of which is incorporated herein by reference. A disposable wearable absorbent article with gender specific indicating can also have primary and secondary indicating.

One or more embodiments of the present disclosure can be combined with one or more embodiments of U.S. non-provisional patent application entitled "Absorbent Articles with Primary and Secondary Indicia," filed on Dec. 23, 2009 under Ser. No. 12/646,430, which is incorporated herein by reference. A disposable wearable absorbent article with gender specific indicating can also have primary and secondary indicia.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable wearable absorbent article, comprising:
a longitudinal centerline;
a male visual wetness indicating area that is a visual fullness indicator associated with a male gender, comprising a plurality of discrete indicators, configured to change from an initial visual state to a subsequent visual state when indicating the presence of a bodily exudates and to indicate degrees of fullness in the absorbent article for liquid body exudates received from a male wearer; and that is substantially elongated along its length, and
a female visual wetness indicating area that is a visual fullness indicator associated with a female gender, comprising a plurality of discrete indicators, configured to change to a subsequent visual state when indicating the presence of a bodily exudates and to indicate degrees of fullness in the absorbent article for liquid body exudates received from a female wearer, and that is substantially elongated along its length;
and wherein the male visual wetness indicating area is configured to change to a first subsequent visual state when indicating the presence of a bodily exudate; and
the female visual wetness indicating area is configured to change to a second subsequent visual state when indicating the presence of a bodily exudate, wherein the second subsequent visual state is visually distinguishable from the first subsequent visual state.

2. The disposable wearable absorbent article of claim 1, wherein:
the male visual wetness indicating area is configured for a male wearer; and
the female visual wetness indicating area is configured for a female wearer.

3. The disposable wearable absorbent article of 1, wherein the male visual wetness indicating area is disposed proximate to the female visual wetness indicating area.

4. The disposable wearable absorbent article of claim 1, wherein the first subsequent visual state is selected from the group including: the color blue, a variation of the color blue, the color green, a variation of the color green, a Mars symbol, an image of a person of male gender, the letter B, the letter M, the word BOY, the word MAN, the word MALE, and combinations thereof.

5. The disposable wearable absorbent article of claim 1, wherein the second subsequent visual state is selected from the group including: the color pink, a variation of the color pink, the color purple, a variation of the color purple, a Venus symbol, an image of a person of female gender, the letter G, the letter W, the letter F, the word GIRL, the word WOMAN, the word FEMALE, and combinations thereof.

6. The disposable wearable absorbent article of claim 1, including a male indicium.

7. The disposable wearable absorbent article of claim 6, wherein the male indicium is disposed proximate to the male visual wetness indicating area.

8. The disposable wearable absorbent article of claim 1, including a female indicium.

9. The disposable wearable absorbent article of claim 8, wherein the female indicium is disposed proximate to the female visual wetness indicating area.

10. The disposable wearable absorbent article of claim 1, wherein:
the male visual fullness indicator has an overall shape with a substantially uniform width; and
the female visual fullness indicator has an overall shape with a substantially uniform width.

11. The disposable wearable absorbent article of claim 1, wherein:
a visual state change at a longitudinally inboard end of the male visual fullness indicator indicates a first degree of fullness for a male wearer; and
a visual state change at a longitudinally inboard end of the female visual fullness indicator indicates a second degree of fullness for a female wearer that is about the same as the first degree of fullness.

12. The disposable wearable absorbent article of claim 1, wherein:
a visual state change at a longitudinally outboard end of the male visual fullness indicator indicates a first degree of fullness for a male wearer; and
a visual state change at a longitudinally outboard end of the female visual fullness indicator indicates a second degree of fullness for a female wearer that is about the same as the first degree of fullness.

13. The disposable wearable absorbent article of claim 1, wherein:
the male visual fullness indicator and the female visual wetness indicator are each disposed in a front of the article;
the article includes a front waist edge;
the male visual fullness indicator includes a longitudinally inboard end disposed at a first longitudinal distance from the front waist edge; and
the female visual fullness indicator includes a longitudinally inboard end disposed at a second longitudinal distance from the front waist edge, wherein the second longitudinal distance is greater than the first longitudinal distance.

14. The disposable wearable absorbent article of claim 1, wherein:
the male visual fullness indicator and the female visual wetness indicator are each disposed in a back of the article;
the article includes a front waist edge;
the male visual fullness indicator includes a longitudinally outboard end disposed at a first longitudinal distance from the front waist edge; and
the female visual fullness indicator includes a longitudinally outboard end disposed at a second longitudinal distance from the front waist edge, wherein the second longitudinal distance is greater than the first longitudinal distance.

15. The disposable wearable absorbent article of claim 1, wherein the male visual fullness indicator and the female visual wetness indicator are each disposed in a front of the article.

16. The disposable wearable absorbent article of claim 1, wherein the male visual fullness indicator and the female visual wetness indicator are each disposed in a back of the article.

17. The disposable wearable absorbent article of claim 1, wherein the male visual fullness indicator and the female visual fullness indicator are substantially elongated along the longitudinal centerline of the article.

18. The disposable wearable absorbent article of claim 1, wherein the male visual fullness indicator and the female visual fullness indicator change from the initial visual state to a subsequent visual state progressively along the length.

* * * * *